(12) United States Patent
Bae et al.

(10) Patent No.: US 8,221,703 B2
(45) Date of Patent: Jul. 17, 2012

(54) DEVICE FOR COLLECTING SAMPLE (75) Inventors: Byeong-Woo Bae, Anyang (KR);
Sung-Dong Lee, Anyang (KR);
Byung-Hoon Kho, Seongnam (KR);
Ji-Eon Ryu, Anyang (KR); Jin-Kyeong Kim, Gunpo (KR); Hyou-Arm Joung, Uiwang (KR); Ku-Cheol Ahn, Anyang (KR)

(73) Assignee: Infopia Co., Ltd. (KR)

( * ) Notice: Subject to any disclaimer, the term of this patent is extended or adjusted under 35 U.S.C. 154(b) by 138 days.

(21) Appl. No.: 12/722,165

(22) Filed: Mar. 11, 2010

(65) Prior Publication Data

US 2010/0304475 A1 Dec. 2, 2010

(30) Foreign Application Priority Data

Jun. 2, 2009 (KR) ........................ 10-2009-0048804

(51) Int. Cl.
*A61B 10/00* (2006.01)
(52) U.S. Cl. ........................................................ 422/536
(58) Field of Classification Search ................... 422/536
See application file for complete search history.

(56) References Cited

U.S. PATENT DOCUMENTS

| | | | |
|---|---|---|---|
| 4,088,448 A | 5/1978 | Lilja et al. | |
| 4,654,197 A | 3/1987 | Lilja et al. | |
| 5,286,454 A | 2/1994 | Nilsson et al. | |
| 5,674,457 A | 10/1997 | Williamsson et al. | |
| 6,447,657 B1 * | 9/2002 | Bhullar et al. | 204/403.01 |
| 2009/0185957 A1 | 7/2009 | Assmann et al. | |

FOREIGN PATENT DOCUMENTS

| | | |
|---|---|---|
| JP | 2000500671 | 1/2000 |
| JP | 2008157708 | 7/2008 |
| KR | 1019990063438 | 7/1999 |
| KR | 1020070009732 | 1/2007 |
| WO | WO 2005110227 A1 * | 11/2005 |

OTHER PUBLICATIONS

Kijima, T.; Nakakita, M.; Watabe, K. JP2008-157708. Machine English Translation. Download date: Oct. 25, 2011. 16 pages.*
International Search Report for application No. PCT/KR2010/003080 dated Jan. 6, 2011.

* cited by examiner

*Primary Examiner* — Bobby Ramdhanie
(74) *Attorney, Agent, or Firm* — Cantor Colburn LLP (57) ABSTRACT

Disclosed herein is a device for collecting a sample, which is intended to dispense a received sample onto a measurement strip. The device includes a main body and a pair of receiving pieces. The receiving pieces protrude from a first end of the main body in such a way as to be spaced apart from each other while facing each other, and receive the sample by capillary force acting on a space which is defined between the receiving pieces and which is open on right, left and bottom sides. The device allows the received sample to be easily transferred to a reaction zone of a measurement strip, and enables the sample to be completely absorbed by the reaction zone because of capillary force in a receiving area when the device comes into contact with the reaction zone of the strip.

11 Claims, 7 Drawing Sheets

DEVICE FOR COLLECTING SAMPLE

BACKGROUND OF THE INVENTION

1. Field of the Invention

The present invention relates generally to a device for collecting a sample and, more particularly, to a device for collecting a sample, which is intended to dispense a received sample onto a measurement strip.

2. Description of the Related Art

As well known to those skilled in the art, among biometric data measurement devices, there are devices which drop a sample such as blood onto a measurement strip and detect an electrochemical change or a change in color that shows the results of an enzymatic reaction in a reaction zone. Generally, a pipette is used to quantitatively dispense a sample onto the reaction zone of the strip.

However, the pipette is problematic in that its receiving part may suck an excessive volume of sample, and it is difficult to finely adjust the volume of the received solution that is dispensed. In order to solve these problems, a hole is bored at a predetermined height of a capillary tube part of the pipette for receiving a solution, thus controlling the volume of the received solution. However, the pipette is also problematic in that capillary pressure is higher than the force sucking in the sample at the reaction zone, so that the transfer of the solution to the reaction zone may not be done or may be ceased in the middle of the transfer.

Further, the pipette is frequently made of a flexible material. Since the pipette is apt to bend, the received solution may be undesirably discharged and thus using the pipette is inconvenient.

SUMMARY OF THE INVENTION

Accordingly, the present invention has been made keeping in mind the above problems occurring in the prior art, and an object of the present invention is to provide a device for collecting a sample, which is capable of controlling capillary pressure, thus making it easy to suck in a sample and to transfer the received sample to a reaction zone.

Another object of the present invention is to provide a device for collecting a sample, which is capable of accurately controlling the volume of the received sample.

In order to accomplish the above objects, the present invention provides a device for collecting a sample, including a main body, and a pair of receiving pieces protruding from a first end of the main body in such a way as to be spaced apart from each other while facing each other and receiving the sample by capillary force acting on a space which is defined between the receiving pieces and which is open on right, left and bottom sides.

The first end of the main body protrudes in an arc shape, and the pair of receiving pieces protrudes in an arc shape to correspond to a shape of the first end of the main body. The curvature of each of the receiving pieces is set such that an end of the receiving piece matches a hole formed in a reaction zone of a measurement strip and is in slight contact with the reaction zone.

Further, the main body comprises a pair of finger seats which are concavely formed to allow a user to easily hold the main body with his or her finger.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, embodiments of the present invention will be described in detail to help those skilled in the art to easily understand and carry out the present invention.

Figure 1:
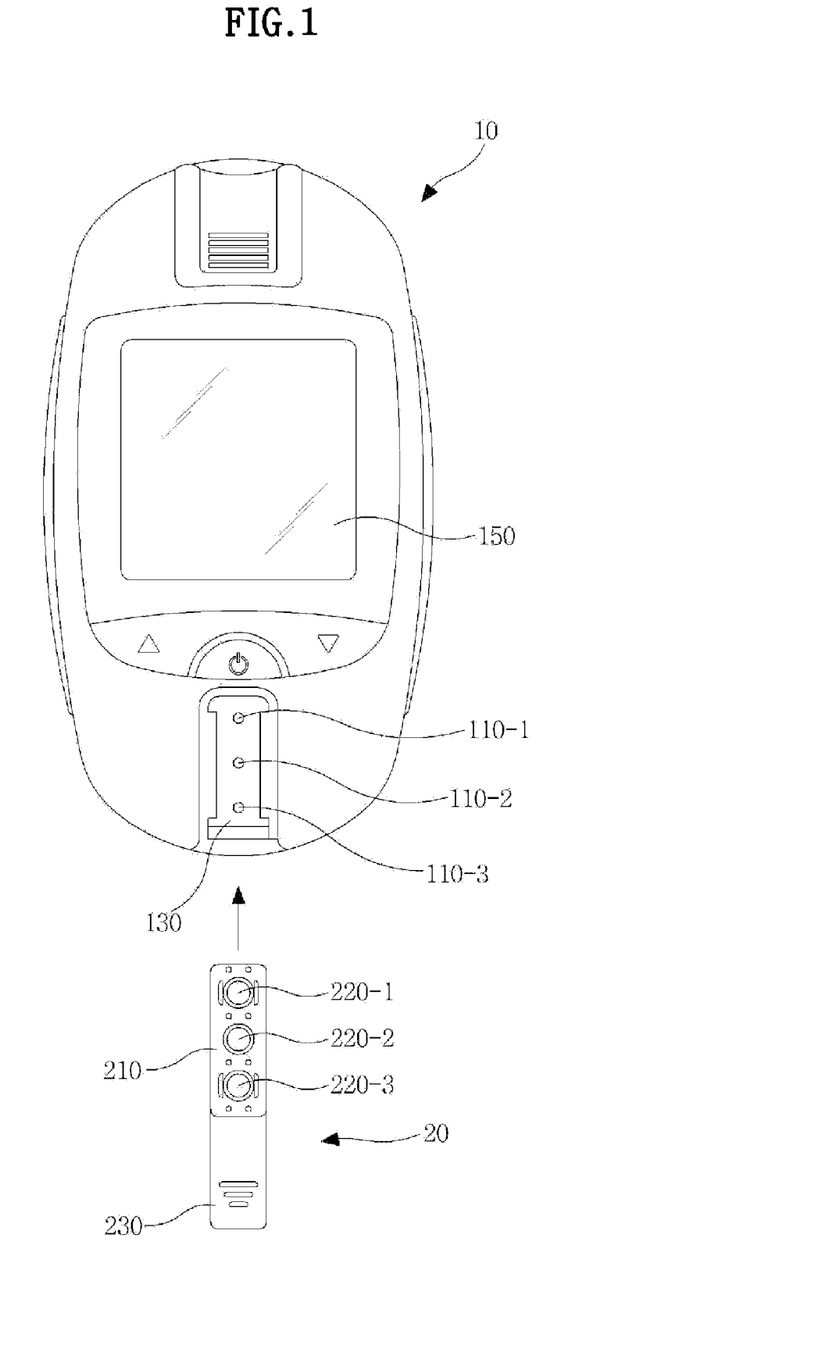
FIG. 1 is a schematic view illustrating a biometric data measurement device and a measurement strip according to an embodiment of the present invention.

FIG. 1 is a schematic view illustrating a biometric data measurement device and a measurement strip according to an embodiment of the present invention. Referring to FIG. 1, the biometric data measurement device 10 includes a power button, a strip insertion part 130, and a display part 150. A groove is formed inside the edge of the strip insertion part 130, thus allowing the measurement strip 20 to be easily inserted into and secured to the strip insertion part 130.

Further, the strip insertion part 130 includes a plurality of sensing parts 110-1, 110-2 and 110-3 which are provided on the central portion of the strip insertion part 130 in such a way that they are spaced apart from each other. The sensing parts 110-1, 110-2 and 110-3 form a one-to-one correspondence with reaction zones of the measurement strip 20. All or some of the sensing parts 110-1, 110-2 and 110-3 are activated according to a measured type, thus sensing the reaction zones of the measurement strip 20.

The measurement strip 20 includes a plurality of reaction zones for measuring biometric data, such as the volume of neutral fat or cholesterol which is present in blood. According to the position of each reaction zone, different data is measured. The measurement strip 20 has on its upper portion a protrusion which is inserted into the groove of the strip insertion part 130, thus enabling the measurement strip 20 to be easily secured to the strip insertion part 130.

Further, the measurement strip 20 includes an upper support 210 and a lower support 230 which are coupled to each other. The reaction zones are provided between the upper support 210 and the lower support 230, and comprise paper to which a catalyst is coupled. The upper support 210 includes holes 220-1, 220-2 and 220-3 through which a portion of a reaction part, namely, the reaction zones, are exposed, so that a sample such as bodily fluid can be applied to the reaction zones and produce a biological response. Here, the predetermined angles with respect to the reaction zones.

In order to perform reaction in the reaction zones of the measurement strip 20, a reaction solution such as blood must be accurately injected into the reaction zones.

Conventionally, bodily fluid such as collected blood has been injected using a pipette. In the case of using a pipette, an excessive volume may be injected into the reaction zones and it is difficult to control a dispensing volume. Further, since the capillary pressure of the pipette is higher than the pressure of the reaction zones, the solution may not be transferred into the reaction zones, or the transfer of the solution may be ceased. A device for collecting a sample according to the present invention is proposed to solve these problems.

Hereinafter, a device for collecting a sample according to an embodiment of the present invention will be described in detail.

Figure 2:
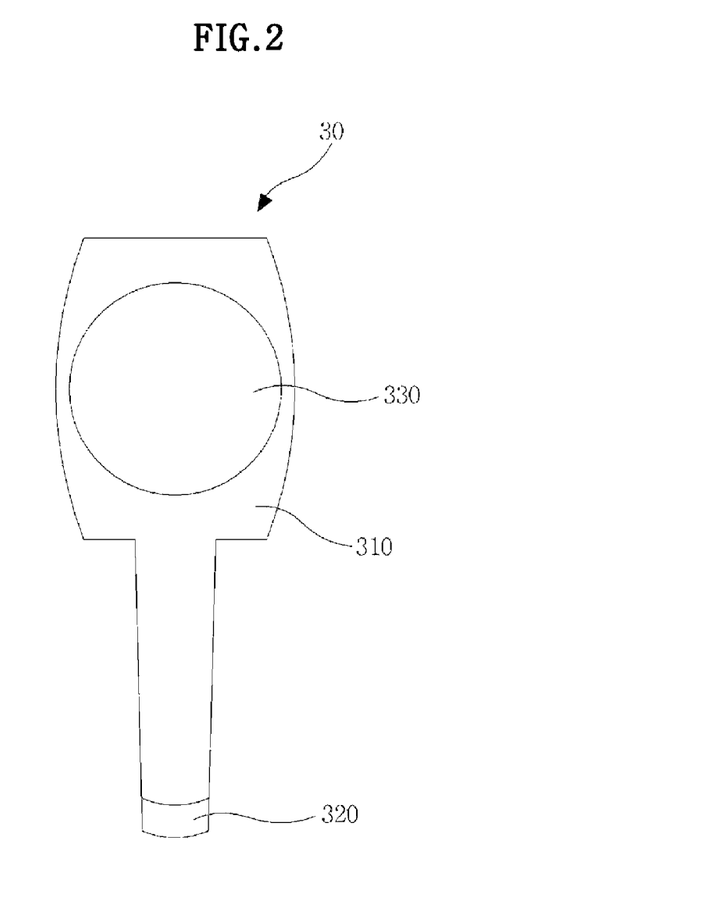
FIG. 2 is a front view illustrating a device for collecting a sample according to an embodiment of the present invention.
Figure 3:
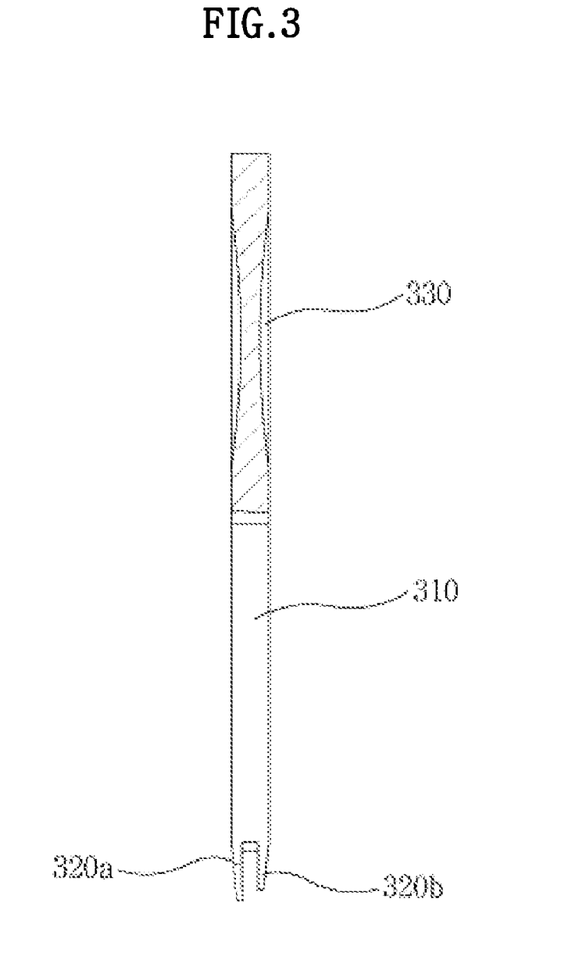
FIG. 3 is a side view illustrating the sample collecting device of FIG. 2.

FIG. 2 is a front view illustrating a device for collecting a sample according to an embodiment of the present invention, and FIG. 3 is a side view illustrating the sample collecting device of FIG. 2.

As shown in the drawings, the sample collecting device 30 according to this embodiment includes a main body 310 and a receiving piece 320.

The main body 310 may be made of an acrylic material. According to this embodiment, the main body 310 includes one pair of finger seats 330 which are formed to be concave to allow a user to easily hold the device 300 with his or her finger. The finger seats 330 allow a user to easily hold the device with his or her thumb and forefinger, thus preventing the sample collecting device from slipping or falling out of his or her hand.

The receiving pieces 320a and 320b are integrated with the main body 310, and protrude from one end of the main body 310 in such a way as to be parallel to each other and be spaced apart from each other, with a space defined between the receiving pieces 320a and 320b to receive a solution. According to this embodiment, the right and left and bottom of the receiving piece 320 are open, thus defining a space which receives the sample by capillary force acting on the space between the receiving pieces 320a and 320b. For example, the receiving piece 320 may be made of an acrylic or plastic material, as is the main body 310.

Further, as shown in FIG. 3, the receiving pieces 320a and 320b are provided to be parallel from and spaced apart from each other, and the right and left and bottom of the space between the receiving pieces are open, thus allowing the sample such as blood to easily flow into a receiving area.

According to this invention, the receiving pieces 320a and 320b may not be parallel to each other but may be formed such that a spacing distance between the receiving pieces 320a and 320b is reduced or increased in a direction distant from the main body 330. Preferably, the spacing distance between the receiving pieces 320a and 320b ranges from 0.20 mm to 2.0 mm.

Further, the receiving area is determined according to the height of the receiving piece 320. Thus, it is possible to control the volume of the received sample by adjusting a width of the receiving piece 320 which protrudes from the main body 310. In this embodiment, the receiving piece 320 is constructed to form the receiving area which may receive a sample of 10 μl or less. That is, the width of the receiving piece 320 is designed to match the volume of the received solution, thus preventing capillary force from being generated because of air being in the space where there is no solution. Thus, the solution received in the receiving area may be easily transferred to the reaction zones of the strip.

Here, the pair of receiving pieces 320a and 320b may differ in height. Although the receiving pieces 320a and 320b have different heights, it is preferable that the difference in height be 3 mm or less.

Further, according to an aspect of the present invention, the first end of the main body 310 protrudes in the shape of an arc, and one pair of receiving pieces 320a and 320b protrudes in the shape of an arc to correspond to the shape of the first end of the main body 310.

Preferably, the receiving piece 320 is formed to be convex in the direction of outflow of the sample, thus allowing the sample, such as bodily fluid, received in a confined space to be easily transferred to the measurement strip.

The curvature of the receiving piece 320 is set such that an end of the receiving piece 320 matches the hole formed in the reaction zone of the measurement strip and makes slight contact with the reaction zone. Here, the receiving piece 320 is inclined to correspond to the shape of the hole of the measurement strip through which the reaction zone is exposed, so that at least a portion of the receiving piece 320 is in contact with the reaction zone of the measurement strip.

Further, according to another aspect of this invention, the inner wall of the receiving piece 320 is treated with a surfactant. Preferably, the inner wall of the receiving piece 320 is treated with a non-ionic surfactant so that red blood cells are not broken. Thereby, the sample such as blood may be more rapidly absorbed between the receiving pieces.

Figure 4:
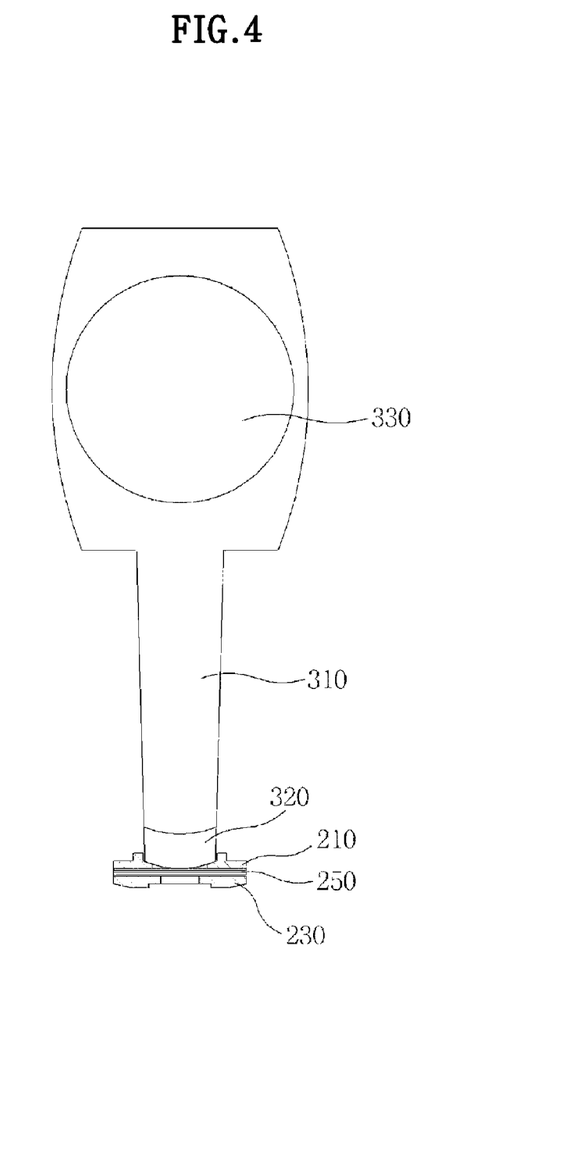
FIG. 4 is a view illustrating the state wherein a receiving piece of the sample collecting device of FIG. 2 comes into contact with a reaction zone of a strip.

FIG. 4 is a view illustrating the state wherein the receiving piece of the sample collecting device of FIG. 2 comes into contact with the reaction zone of the strip.

As shown in FIG. 4, in the sample collecting device according to this embodiment, the receiving piece 320 has a circular shape to match the shape of the hole formed in the upper support 210 of the measurement strip, so that the central portion of the receiving piece 320 is in contact with a reaction part 250 which is inserted between the upper support 210 and the lower support 230. Thus, the sample collecting device enables the reaction part 250 to accurately absorb the received solution.

Since the upper layer of the reaction zone of the strip has good sample dispersion and is dry, the capillary force of the reaction zone of the strip is larger than that of the internal receiving space of the receiving piece 320 of the sample collecting device. Therefore, when the central portion of the receiving piece 320 of the sample collecting device comes into contact with the reaction zone of the strip, the sample between the receiving pieces 320a and 320b can be rapidly transferred to the reaction zone of the strip.

Figure 5:
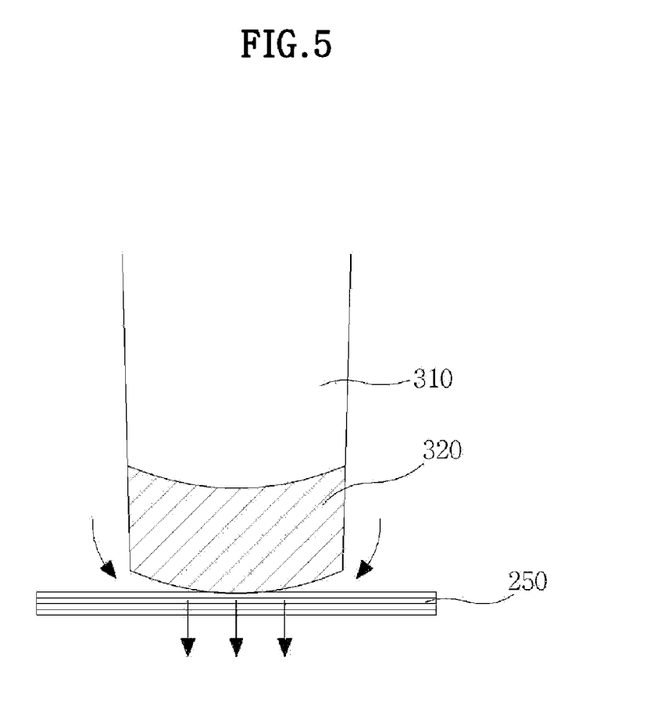
FIG. 5 is a view illustrating the flow of the sample received in the sample collecting device.

FIG. 5 is a view illustrating the flow of the sample received in the sample collecting device. As shown in the drawing, the receiving pieces 320a and 320b protrude to be parallel to and spaced apart from each other, and the bottom and both sides of the receiving space defined by the receiving pieces 320a and 320b are open, thus allowing a sample such as blood to more easily flow into the receiving space. Further, an end of the receiving piece protrudes in the shape of an arc, thus making it easy for the received solution to flow in the direction shown by the arrows. Since the height of the receiving space defined by the receiving pieces 320a and 320b is not high, an excessive increase in capillary force is prevented. Thus, the collected sample of the receiving space can be more smoothly absorbed by the reaction part 250.

Figure 6:
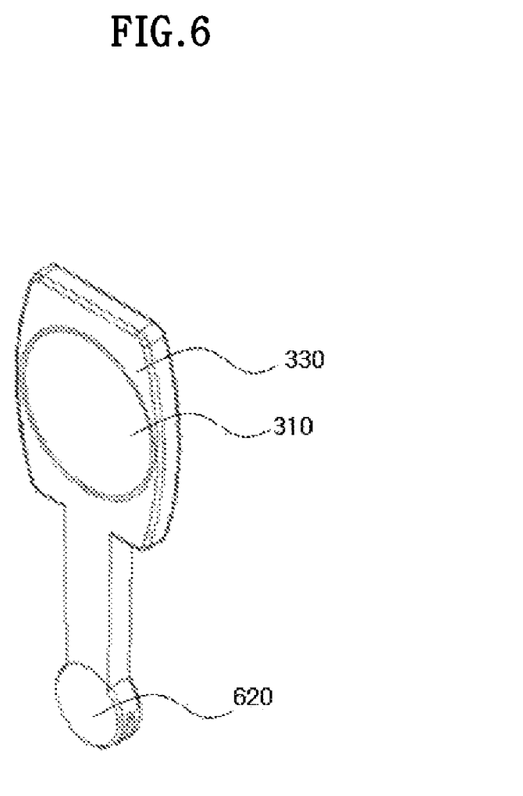
FIG. 6 is a perspective view illustrating a device for collecting a sample according to another embodiment of the present invention.
Figure 7:
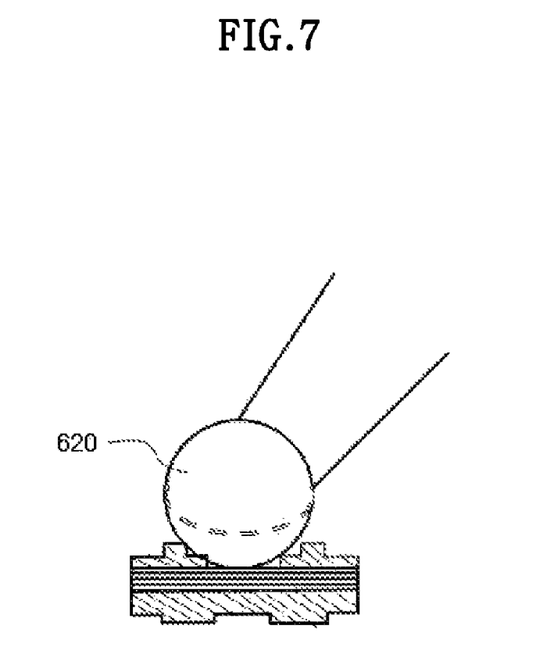
FIG. 7 is a view illustrating the state wherein a receiving piece of the sample collecting device of FIG. 6 comes into contact with a reaction zone of a strip.

FIG. 6 is a perspective view illustrating a device for collecting a sample according to another embodiment of the present invention, and FIG. 7 is a view illustrating the state wherein a receiving piece of the sample collecting device of FIG. 6 comes into contact with a reaction zone of a strip.

Referring to the drawings, the sample collecting device according to another embodiment of the present invention includes a circular receiving piece 620.

As shown in the drawing, the receiving piece 620 has a circular shape, and the width of the receiving piece 620 is variably adjustable, so that the receiving piece 620 may receive a desired sample to the extent of about 20 μl. In the manufacturing process, the width of the receiving piece 620 may be quantitatively determined according to the volume of the received sample.

Further, the receiving piece 620 has the circular shape described above. Thus, as shown in FIG. 7, although the receiving piece 620 obliquely comes into contact with the reaction zone, it is possible to inject the received sample. Since the receiving piece 620 doesn't have to come into contact with the reaction zone in a vertical direction, convenience is improved. According to an embodiment, although the sample collecting device comes into contact with the reaction zone to be inclined to the right or left by 60 degrees with respect to a vertical angle, the received sample can be injected into the reaction zone.

As described above, the present invention provides a device for collecting a sample, which enables the injection of samples such as blood. Further, the sample collecting device allows the received sample to be easily transferred to a reaction zone of a measurement strip, and enables the sample to be completely absorbed by the reaction zone because of capillary force in a receiving area when the device comes into contact with the reaction zone of the strip.

Further, according to the depth of the space for receiving the solution, the volume of the received solution may be variously adjusted, so that it is possible to inject and receive an accurate volume of solution.

Moreover, a sample can be more smoothly absorbed by a receiving area, and the transfer of the received sample to a reaction zone is easy although a sample collecting device receiving the sample is in contact with the reaction zone at various angles.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for collecting a sample, comprising: a main body; and a pair of receiving pieces protruding from a first end of the main body in such a way as to be spaced apart from each other while facing each other, and receiving the sample by capillary force acting on a space which is defined between the receiving pieces and which is open on right, left and bottom sides, wherein a curvature of each of the receiving pieces is configured such that an end of the receiving piece matches a hole formed in a reaction zone of a measurement strip and is in slight contact with the reaction zone.

2. The device as set forth in claim 1, wherein the first end of the main body protrudes in an arc shape, and the pair of receiving pieces protrudes in an arc shape to correspond to a shape of the first end of the main body.

3. The device as set forth in claim 2, wherein an inner wall of each of the receiving pieces is treated with a surfactant.

4. The device as set forth in claim 2, wherein the receiving pieces protrude by different lengths from the main body, and a difference in protruding length between the receiving pieces is 3 mm or less.

5. The device as set forth in claim 2, wherein a spacing distance between the receiving pieces ranges from 0.20 mm to 2.00 mm.

6. The device as set forth in claim 1, wherein the pair of receiving pieces is formed in a circular shape.

7. The device as set forth in claim 6, wherein an inner wall of each of the receiving pieces is treated with a surfactant.

8. The device as set forth in claim 6, wherein the receiving pieces protrude by different lengths from the main body, and a difference in protruding length between the receiving pieces is 3 mm or less.

9. The device as set forth in claim 6, wherein a spacing distance between the receiving pieces ranges from 0.20 mm to 2.00 mm.

10. The device as set forth in claim 1, wherein the main body comprises a pair of finger seats which are concavely formed on a second end of the main body to allow a user to easily hold the main body with his or her finger.

11. The device as set forth in claim 1, wherein the sample collecting device is made of an acrylic or hydrophilic plastic material.

* * * * *